United States Patent [19]

Hirai et al.

[11] Patent Number: 5,547,329
[45] Date of Patent: Aug. 20, 1996

[54] ROLLER BOTTLE HANDLING SYSTEM

[75] Inventors: Osamu Hirai; Keiji Tamura; Hajime Ichihashi, all of Tokyo-to, Japan

[73] Assignee: Kirin Beer Kabushiki Kaisha, Tokyo-to, Japan

[21] Appl. No.: 418,294

[22] Filed: Apr. 7, 1995

[30] Foreign Application Priority Data

Jun. 22, 1994 [JP] Japan .................................. 6-140410

[51] Int. Cl.⁶ ...................................................... B65G 1/10
[52] U.S. Cl. ............................. 414/222; 53/246; 53/251; 53/534; 53/50; 414/331
[58] Field of Search .................. 414/267, 331, 414/411, 416, 222; 53/50, 246, 251, 252, 492, 534, 381.1

[56] References Cited

U.S. PATENT DOCUMENTS

| | | | |
|---|---|---|---|
| 2,718,972 | 9/1955 | Temple | 414/331 X |
| 4,634,333 | 1/1987 | Butterly, Jr. et al. | 414/331 |
| 4,669,047 | 5/1987 | Chucta | 414/331 X |
| 4,797,989 | 1/1989 | Cherko | 414/222 X |
| 4,982,553 | 1/1991 | Itoh | 414/222 X |
| 5,228,820 | 7/1993 | Stansfield et al. | 414/331 X |
| 5,277,229 | 1/1994 | Kikuchi et al. | 414/331 X |
| 5,287,895 | 2/1994 | Raaijmakers et al. | 414/222 X |
| 5,310,300 | 5/1994 | Crabb et al. | 414/331 X |
| 5,333,983 | 8/1994 | Hatouchi et al. | 414/331 |
| 5,411,151 | 5/1995 | Sasada | 414/331 |

FOREIGN PATENT DOCUMENTS

| | | | |
|---|---|---|---|
| 60-161825 | 8/1985 | Japan | 414/331 |
| 64-23833 | 1/1989 | Japan . | |

*Primary Examiner*—David A. Bucci
*Attorney, Agent, or Firm*—Oblon, Spivak, McClelland, Maier & Neustadt, P.C.

[57] ABSTRACT

A roller bottle handling system includes a culture rack storage station for storing a plurality of culture racks each for accommodating a plurality of roller bottles each filled with a culture medium and cells, and a mass-handling facility for extracting completed cultures from roller bottles and replacing a culture medium in the roller bottles with a new culture medium. The roller bottle handling system further includes an unloading station for taking out roller bottles from culture racks delivered from the culture rack storage station and delivering the roller bottles to the mass-handling facility, and a loading station for charging roller bottles filled with a culture medium and cells into culture racks. Automatic guided vehicles or overhead traveling cranes are movable to deliver culture racks, one at a time, between the culture rack storage station and the unloading and loading stations. Aerial carriages run along elevated tracks to deliver culture racks, one at a time, between the unloading station and the loading station.

18 Claims, 9 Drawing Sheets

ROLLER BOTTLE HANDLING SYSTEM

BACKGROUND OF THE INVENTION

1. Field of the Invention

The present invention relates to a roller bottle handling system for handling roller bottles stored in culture racks and used as containers for culturing adhesive animal cells, and more particularly to a roller bottle handling system which can handle the roller bottles, rack by rack, for thereby automatizing a process of culturing adhesive animal cells in the roller bottles.

2. Description of the Prior Art

According to rearing pattern, animal cells are classified into two types, one of which is animal cells which adhere to a wall surface and are cultured, the other of which is animal cells which are suspended in culture medium and cultured. One known process of culturing adhesive (or periphytic) animal cells uses a large number of roller bottles for culturing animal cells therein. This method of using roller bottles is advantageous, compared with a method of using a large tank, in that the effective area of wall surface to which the animal cells adhere is large. This method of using roller bottles is also advantageous, compared with a method of using a large tank, in that in case of mixing of foreign matters such as unnecessary bacteria into animal cells to be cultured, only animal cells in a roller bottle which contains foreign matters are required to be disposed of, while all animal cells in the tank are required to be disposed of. Therefore, the method of using roller bottles is preferably applied to a culture of adhesive animal cells. There has been developed a system for automatically handling such a large number of roller bottles by storing roller bottles in a culture rack, taking out roller bottles with completed cultures from the culture rack, extracting the cultures from the roller bottles, and filling roller bottles with animal cells to be newly cultured. Generally, a roller bottle handling system employs rotary culture racks for holding roller bottles that are filled with animal cells and a culture medium. One conventional example of such a roller bottle handling system is disclosed in Japanese laid-open patent publication No. 64-23883.

In the disclosed roller bottle handling system, animal cells are cultured in roller bottles that are stored in an endless array of rotary culture racks which rotate on a track. The roller bottle handling system basically includes a turning mechanism for turning down bottles which have been delivered and erected on a conveyor, a pushing mechanism for pushing roller bottles toward a culture rack to automatically insert the roller bottles into the culture rack, and an erecting mechanism for pushing roller bottles with completed cultures out of the culture rack and then erecting the roller bottles. The roller bottle handling system allows automatization of the various steps of storing roller bottles, filling roller bottles with a culture medium, and inoculating cells into the culture medium in the roller bottles, so that a large number of roller bottles can be handled without human intervention.

In the conventional roller bottle handling system, however, since a succession of culture racks are connected into an annular rack assembly, when one of the culture rack happens to suffer some trouble, it cannot easily be isolated and removed out of the roller bottle handling system. Therefore, the conventional roller bottle handling system is not sufficiently flexible and cannot be quickly recovered from failures of individual culture racks.

Another problem with the rotary culture racks is that any roller bottles stored in a culture rack cannot easily be removed upon demand or inspected daily. This is because a succession of culture racks are connected into an annular rack assembly, and an operator cannot access roller bottles in the culture rack from a backside thereof, but can access the roller bottles only from a front side thereof in the conventional roller bottle handling system.

SUMMARY OF THE INVENTION

It is therefore an object of the present invention to provide a roller bottle handling system which is capable of allowing roller bottles stored in culture racks to be easily inspected daily and to be replaced rack by rack, so that the roller bottles can be handled flexibly and quickly.

According to the present invention, the above object can be accomplished by a roller bottle handling system comprising a culture rack storage station for storing a plurality of culture racks each for accommodating a plurality of roller bottles each filled with a culture medium and cells, a mass-handling facility for extracting completed cultures from roller bottles and replacing culture medium in the roller bottles with a new culture medium, an unloading station for unloading roller bottles from culture racks delivered from the culture rack storage station and delivering the unloaded roller bottles to the mass-handling facility, a loading station for loading roller bottles filled with culture medium and cells into culture racks, first conveying means for conveying culture racks, one at a time, between the culture rack storage station and the unloading and loading stations, and second conveying means for conveying culture racks, one at a time, between the unloading station and the loading station.

The first conveying means may comprise an automatic guided vehicle or an overhead traveling crane.

The second conveying means may comprise an aerial carriage movable along an elevated track.

It is preferable that culture racks be arranged in a number of arrays directly on a floor in the culture rack storage station.

The first and second conveying means may be common means comprising, for example, an automatic guided vehicle.

According to the present invention, a culture rack which stores roller bottles with completed cultures is delivered from the culture rack storage station to the unloading station by the first conveying means. In the unloading station, the roller bottles with completed cultures are taken out from the culture rack. The empty culture rack is then delivered to the loading station by the second conveying means. In the loading station, the empty culture rack waits for roller bottles to be delivered from the mass-handling facility where cultures are extracted from the roller bottles, the culture medium is replaced with a new culture medium, and cells are inoculated into the roller bottles.

After the roller bottles delivered from the mass-handling facility are loaded into the empty culture rack, the culture rack is transferred to the first conveying means, and delivered thereby to a predetermined location in the culture rack storage station.

The roller bottle handling system can automatize a process of handling roller bottles rack by rack, i.e., can automatically carry out the various steps of delivering culture racks into and out of the culture rack storage station, taking out roller bottles from culture racks, loading roller bottles into culture racks, extracting cultures from roller bottles, cleaning roller bottles, and filling a culture medium and cells in roller bottles. As a consequence, the roller bottle handling system can handle a large number of roller bottles automatically.

In the culture rack storage station, culture racks are positioned in neat arrays on the floor, and the cells in the roller bottles are cultured. While the cells in the roller bottles are being cultured, they are periodically inspected for any trouble by an operator. In the event of some accident happening on any one of the culture racks or the roller bottles stored therein, since the roller bottles are stored in the culture racks, only the culture rack which is encountering problems or contains a problem roller bottle or bottles can quickly be removed out of the roller bottle handling system without shutting off the entire roller bottle handling system.

The above and other objects, features, and advantages of the present invention will become apparent from the following description when taken in conjunction with the accompanying drawings which illustrate preferred embodiments of the present invention by way of example.

DESCRIPTION OF THE PREFERRED EMBODIMENTS

Figure 1:
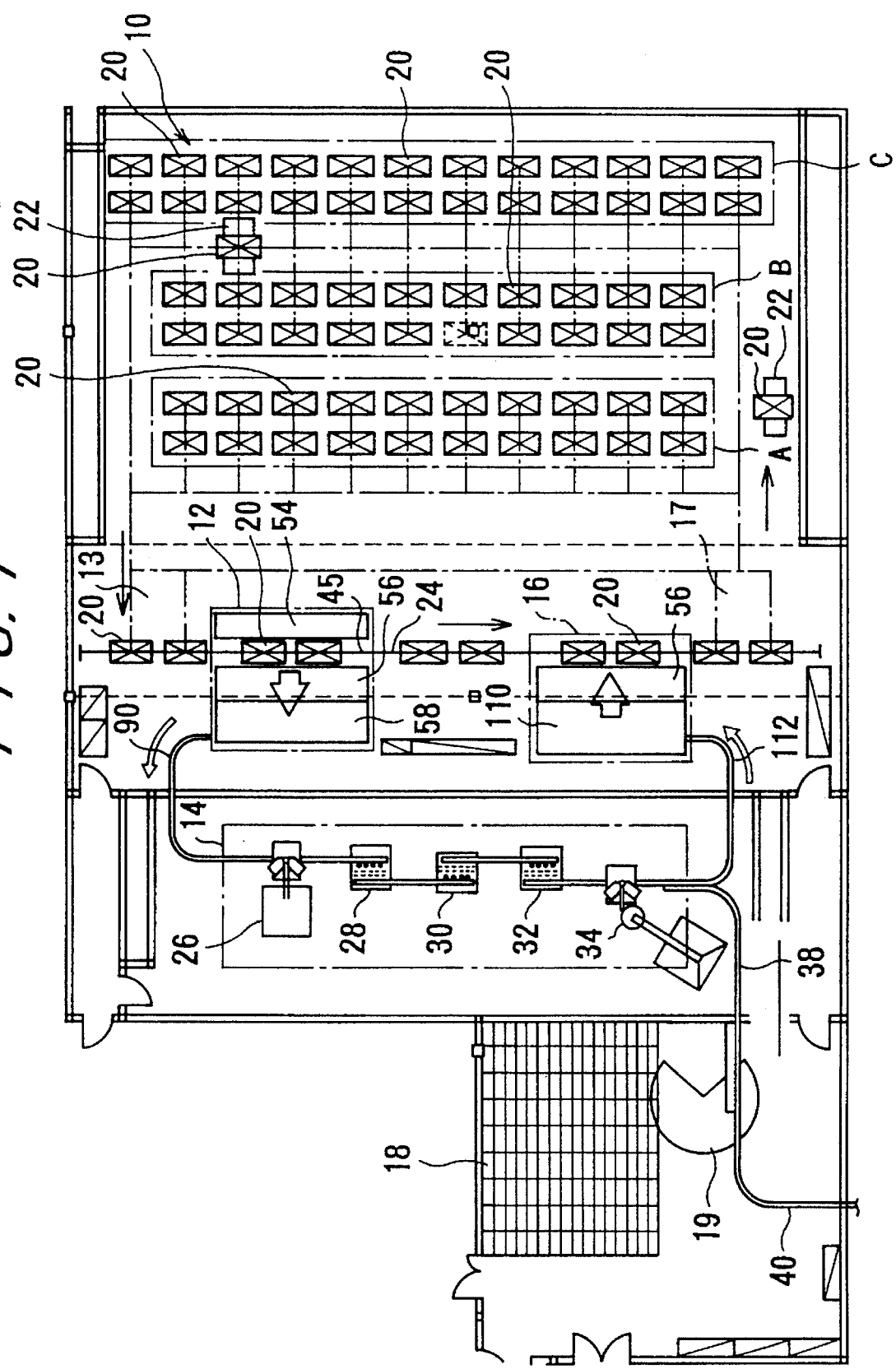
FIG. 1 is a plan view of a roller bottle handling system according to a first embodiment of the present invention.
Figure 2:
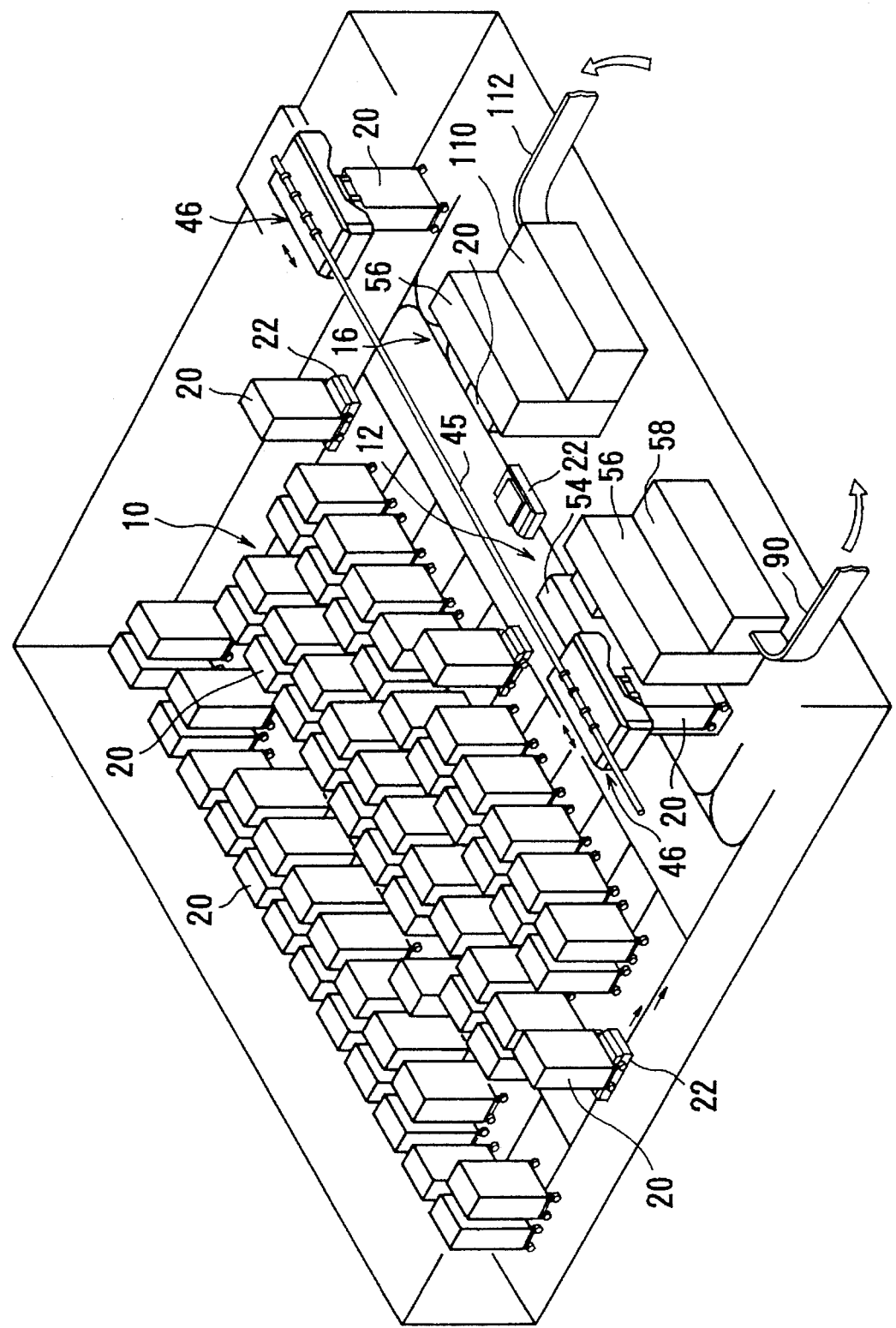
FIG. 2 is a perspective view of the roller bottle handling system shown in FIG. 1.

A roller bottle handling system according to a first embodiment of the present invention will be described with reference to FIGS. 1 through 7. As shown in FIGS. 1 and 2, the roller bottle handling system comprises a culture rack storage station 10 for storing a number of culture racks 20 each holding a plurality of roller bottles that are filled with a culture medium and a culture solution for culturing adhesive animal cells which are inoculated. In the culture rack storage station 10, the culture racks 20 are erected and arranged in a number of arrays directly on a floor, and passageways are defined between the arrays of culture racks 20 for allowing carriages to run therealong to deliver culture racks 20 into and out of the culture rack storage station 10.

The roller bottle handling system also comprises an unloading station 12 for taking out roller bottles from a culture rack 20 and supplying the roller bottles to a conveyor 90, a mass-handling facility 14 (see FIG. 1) for extracting cultured cells from roller bottles and filling roller bottles with cells and a culture medium, and a loading station 16 for loading roller bottles with replaced cells and culture medium into a culture rack 20. The unloading station 12 and the loading station 16 are positioned adjacent to each other, and interposed between the culture rack storage station 10 and the mass-handling facility 14. The unloading station 12 will be described in detail later on with reference to FIG. 5, and the loading station 16 will be described in detail later on with reference to FIG. 7.

The culture racks 20 are carried by automatic guided vehicles 22 which run along the passageways between the arrays of culture racks 20 to deliver the culture racks 20 into and out of the culture rack storage station 10 in the direction indicated by the arrows in FIG. 1. To deliver a culture rack 20 out of the culture rack storage station 10, the culture rack 20 is placed on an automatic guided vehicle 22 and carried thereby in the culture rack storage station 10 up to a first transfer station 13 that is positioned next to and upstream of the unloading station 12. The culture rack 20 is then delivered from the first transfer station 13 to the unloading station 12 by an aerial carriage (described later on). In the unloading station 12, all the roller bottles are taken out from the culture rack 20. The empty culture rack 20 is thereafter carried by an aerial carriage along a delivery line 24 to the loading station 16 where it waits for roller bottles from the mass-handling facility 14. In the mass-handling facility 14, cultivated cells are extracted from roller bottles, the empty roller bottles are cleaned, and filled with a culture medium and cells. After the roller bottles from the mass-handling facility 14 are transferred to the culture rack 20 at the loading station 16, the culture rack 20 is fed from the loading station 16 by an aerial carriage to a second transfer station 17 which is positioned next to and downstream of the loading station 16. In the second transfer station 17, the culture rack 20 is transferred from the aerial carriage onto an automatic guided vehicle 22. The culture rack 20 is then delivered by the automatic guided vehicle 22 to a predetermined location in the culture rack storage station 10.

As shown in FIG. 1, the roller bottle handling system also includes a bottle storage area 18 where spare roller bottles are stocked. Empty roller bottles can be supplied from the bottle storage area 18 by a transfer unit 19 through a supply line 38 to the mass-handling facility 14. Used roller bottles can be discharged from the mass-handling facility 14 through a discharge conveyor 40.

Details of the roller bottle handling system will be described below with reference to FIGS. 3 through 7.

Figure 3:
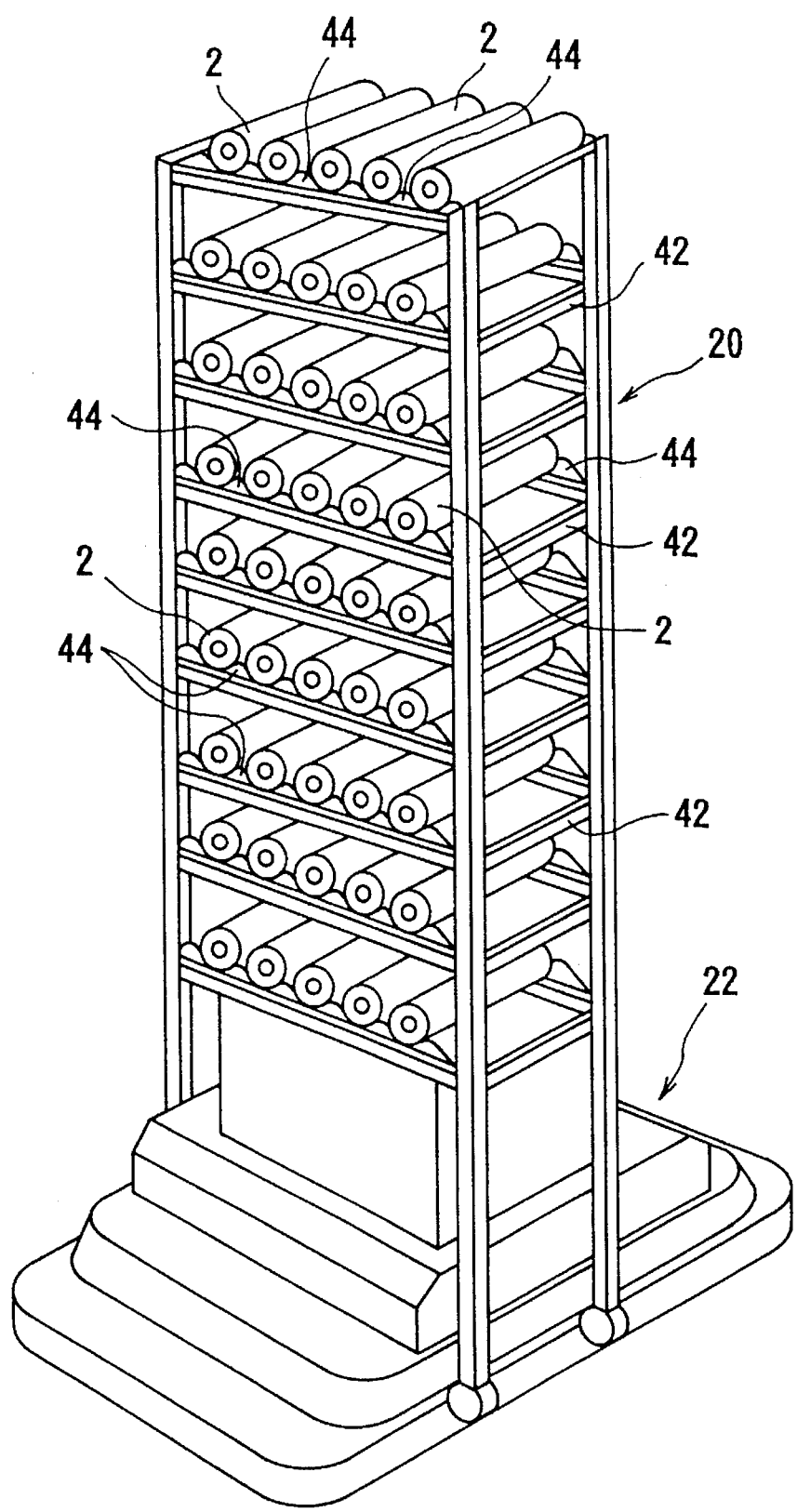
FIG. 3 is a perspective view of a culture rack storing roller bottles and an automatic guided vehicle.

FIG. 3 shows a culture rack 20 and an automatic guided vehicle 22 which carries and delivers the culture rack 20. The culture rack 20 has a vertical array of culture shelves 42 each storing roller bottles 2 horizontally. In each of the culture shelves 42, the roller bottles 2 are horizontally spaced at constant intervals by positioning members or spacers 44 for easy insertion into and removal from the culture rack 20. The roller bottles 2 can be inserted into and taken out from the culture rack 20 in the direction along the axes of the roller bottles 2. The roller bottles 2 are rotated around their own axes at a predetermined speed during cultivation.

The automatic guided vehicle 22 is of the known type which is used in conventional material-handling systems and remotely controllable for movement along passageways. In the culture rack storage station 10, the automatic guided vehicle 22 is self-propelled along the passageways between the arrays of culture racks 22, and can be stopped at any storage location.

Figure 4:
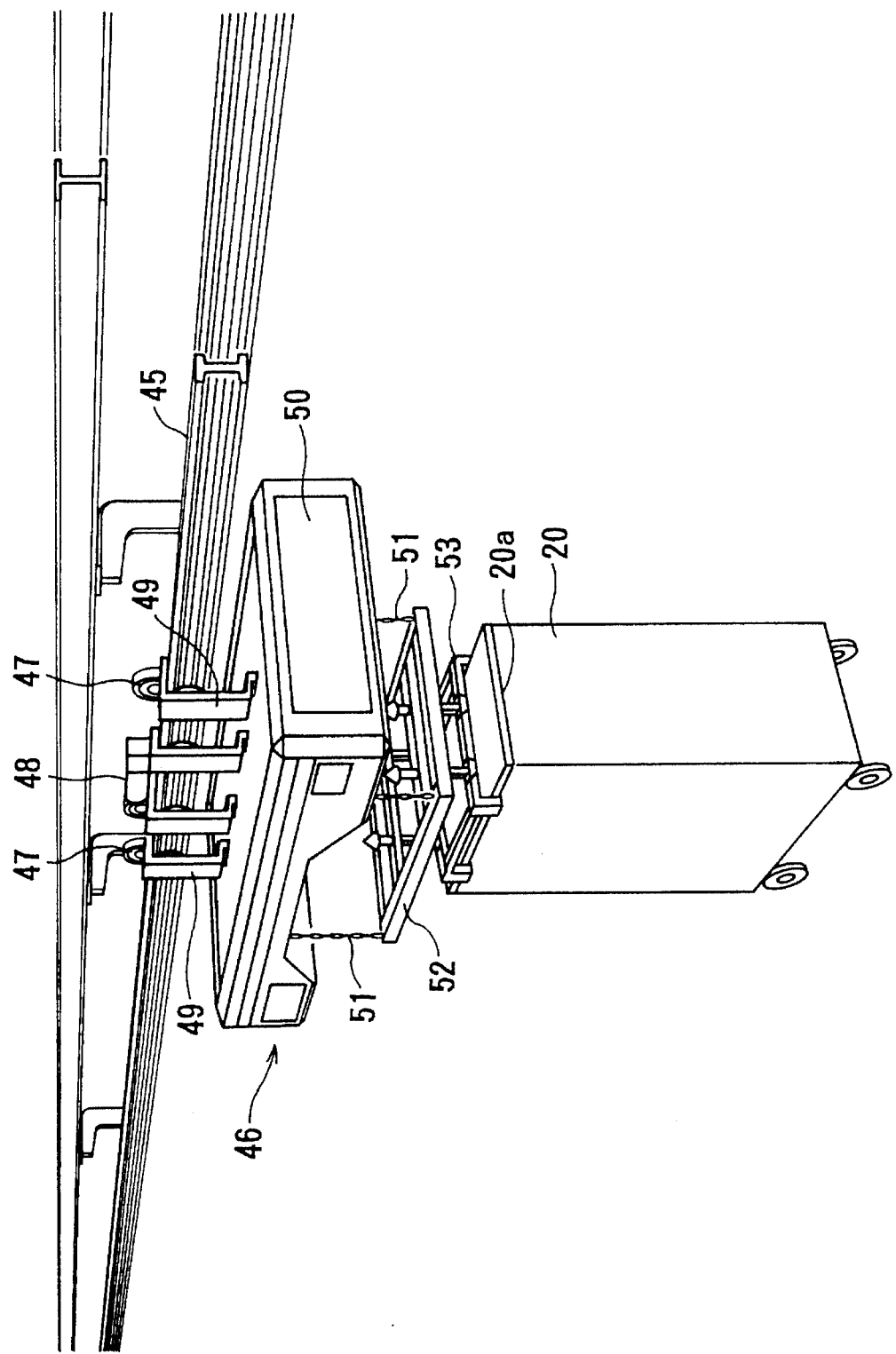
FIG. 4 is a perspective view of an aerial carriage.

The first transfer station 13 serves to transfer the culture rack 20 delivered thereto by the automatic guided vehicle 22 onto an aerial carriage 46 shown in FIG. 4. As shown in FIG. 4, the aerial carriage 46 runs along an elevated track 45 which extends along the delivery line 24 (FIG. 1). The aerial carriage 46 basically comprises a driving unit 48 for rotating rollers 47 on the elevated track 45, and a carriage body 50 suspended from the driving unit 48 by suspension arms 49. A support frame 52 depends from the carriage body 50 through chains 51, and grip arms 53 are disposed below and connected to the support frame 52. The grip arms 53 detachably engage a top plate 20a of the culture rack 20. The culture rack 20 is delivered along the elevated track 45 while being suspended by the aerial carriage 46.

Figure 5:
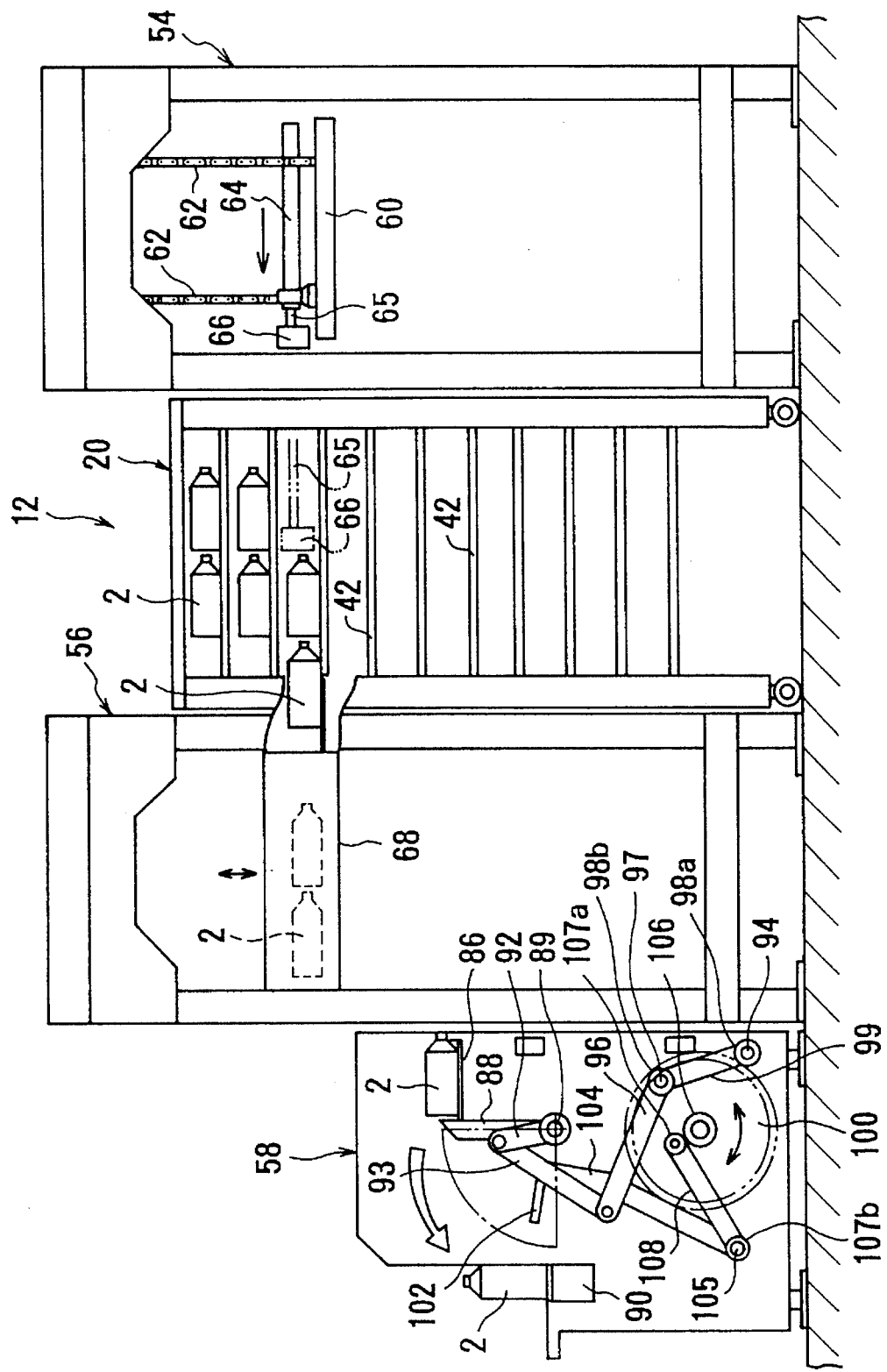
FIG. 5 is a side elevational view of a roller bottle pusher device, a roller bottle transfer device, and a roller bottle discharger in an unloading station.

As shown in FIG. 5, the unloading station 12 comprises a roller bottle pusher device 54 for simultaneously pushing roller bottles 2 forwardly (to the left in FIG. 5) out of one, at a time, of the culture shelves 42 of the culture rack 20, a roller bottle transfer device 56 having a vertically movable bed unit 68 for moving roller bottles forwardly, and a roller bottle discharger 58 for turning roller bottles transferred by the roller bottle transfer device 56 from a horizontal position to a vertical position and supplying the roller bottles thus erected to the conveyor 90. The culture rack 20 is brought by the aerial carriage 46 into a position between the roller bottle pusher device 54 and the roller bottle transfer device 56. The roller bottle discharger 58 is positioned adjacent to the roller bottle transfer device 56 remotely from the roller bottle pusher device 54.

The roller bottle pusher device 54 comprises a horizontal table 60 vertically movably suspended by chains 62, and a horizontal pusher cylinder 64 mounted on the table 60 for pushing roller bottles 2. The pusher cylinder 64 has a piston rod 65 with a pusher plate 66 attached to its distal end. When the pusher cylinder 64 is actuated to extend the piston rod 65 as indicated by the arrow in FIG. 5, the pusher plate 66 engages all the roller bottles 2 arrayed in one, at a time, of the culture shelves 42 and push them simultaneously out of the culture shelf 42 into the roller bottle transfer device 56.

The vertically movable bed unit 68 of the roller bottle transfer device 56 can receive the roller bottles 2 pushed out of the culture shelf 42 by the roller bottle pusher device 54 at the time when the vertically movable bed unit 68 is vertically positioned in horizontal alignment with the culture shelf 42.

Figure 6:
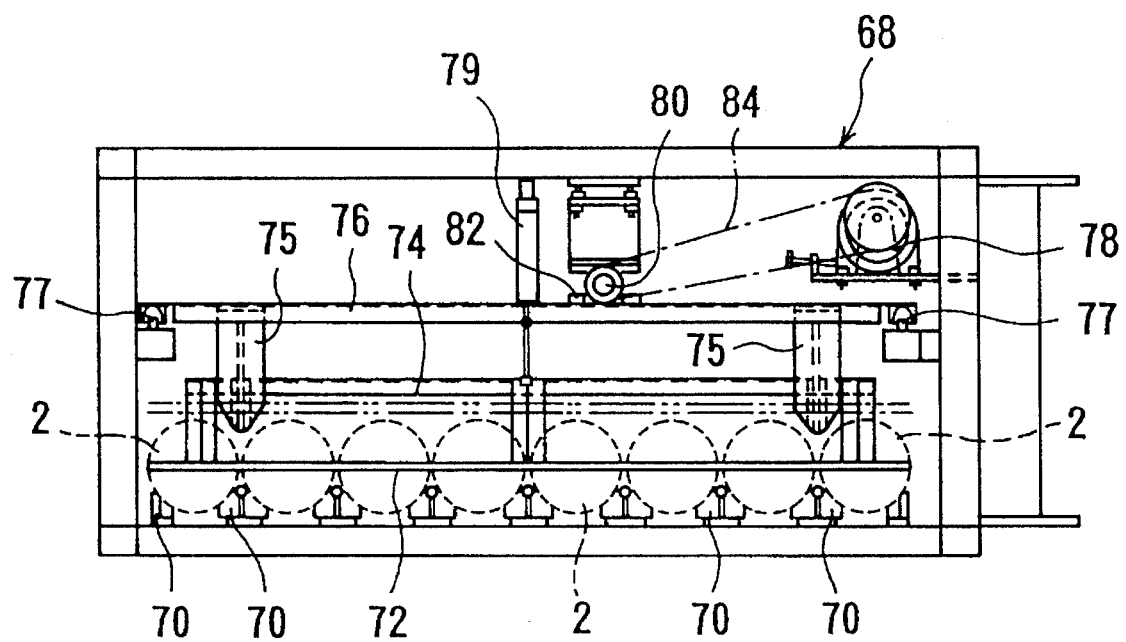
FIG. 6 is a front elevational view of the bed of the bottle transfer device.

As shown in FIG. 6, the vertically movable bed unit 68 has a plurality of equally spaced guides 70 for receiving the supplied roller bottles 2 at constant intervals. Each of the guides 70 comprises a substantially triangular member having a pair of upper side surfaces each extending arcuately substantially along a quarter arc. Each of the roller bottles 2 can be supported between the confronting and spaced arcuate upper side surfaces of two adjacent guides 70 which are spaced at an interval corresponding to the outside diameter of the roller bottle 2. In the illustrated embodiment, the bed unit 68 can receive a maximum of eight roller bottles 2 at a time.

The roller bottles 2 transferred onto the bed unit 68 can be pushed axially toward the roller bottle discharger 58 by a bottle pusher 72 which is long enough to cover the array of roller bottles 2 on the bed unit 68. Specifically, the bottle pusher 72 is mounted on a portal-shaped frame 74 that hangs downwardly from a movable base 76 through support members 75. The movable base 76 is connected to a vertical cylinder 79 so as to be movable vertically. The bottle pusher 72 is positioned at an upper position when the roller bottles 2 are pushed onto the guides 70. After the roller bottles 2 are placed on the guides 70, the bottle pusher 72 is positioned at a lower position. The movable base 76 is also movable along guide rails 77 in the axial direction of the roller bottles 2 by a motor 78. The motor 78 is operatively coupled by a chain 84 to a worm 80 that is held in mesh with a rack 82 mounted on the movable base 76, so that when the motor 78 is energized, the worm 80 is rotated, thus moving the rack 82 and hence the movable base 76. After the roller bottles 2 have been inserted into the bed unit 68, the bed unit 68 is vertically moved into horizontal alignment with a receiver base 86 of the roller bottle discharger 58 for transfer of the roller bottles 2 into the roller bottle discharger 58.

The roller bottle discharger 58 will be described below with reference to FIG. 5. The roller bottles 2 pushed from the roller bottle transfer device 56 are first placed on the receiver base 86. The receiver base 86 is supported on a swing arm 88 that is mounted on a shaft 89 for swinging movement through 90° between a vertical position (indicated by the solid lines) and a horizontal position (indicated by the dot-and-dash lines). To the swing arm 88, there is integrally coupled a crank arm 92 which is operatively connected through a link 93 to a swing link 96. The swing link 96 can be rotated about the shaft 97 by a torque transmitting mechanism which comprises a gear 98a mounted on a shaft 94, a gear 98b mounted on a shaft 97, and a chain 99 trained around the gears 98a and 98b. The gear 98a is held in mesh with a large gear 100 which can be rotated by an actuator (not shown).

The roller bottle discharger 58 also has a pusher mechanism for pushing erected roller bottles 2 from the receiver base 86 toward the conveyor 90. The pusher mechanism comprises a link 104 having a right-angularly bent pusher 102 on its distal end and swingably supported on a shaft 105. The link 104 can be rotated about the shaft 105 by a torque transmitting mechanism which comprises a gear 107a meshing with a small gear 106 that is concentrically rotatable in unison with the large gear 100, a gear 107b mounted on a shaft 105, and a chain 108 trained around the gears 107a and 107b.

When the large gear 100 rotates clockwise in FIG. 5, the swing link 96 lowers the swing arm 88 with the roller bottles 2 from the vertical position to the horizontal position. The roller bottles 2 placed in the erected position on the receiver base 86 are then pushed by the pusher 102 onto the conveyor 90 by the link 104 which is angularly moved forwardly about the shaft 105.

The roller bottles 2 thus supplied to the conveyor 90 are then delivered to the mass-handling facility 14. As shown in FIG. 1, the mass-handling facility 14 comprises a cap removing device 26, a culture medium drawing device 28, a bottle cleaning device 30, a culture medium filling device 32, and a cap tightening device 34, which are successively arranged downstream in the direction in which roller bottles 2 move through the mass-handling facility 14. While roller bottles 2 are continuously fed through the mass-handling facility 14 by the conveyor 90, the caps are removed from the roller bottles 2 by the cap removing device 26, and then the cultured cells are extracted from the roller bottles 2 by the culture medium drawing device 28. Thereafter, the inner surfaces of the empty roller bottles 2 are cleaned by the bottle cleaning device 30, and a new culture medium is filled in the roller bottles 2 and cells to be cultured are inoculated into the roller bottles 2 by the culture medium filling device 32. The caps are attached to the roller bottles 2 by the cap tightening device 34. The roller bottles 2 with the replaced culture medium and cells are then delivered to the loading station 16 by a conveyor 112.

Figure 7:
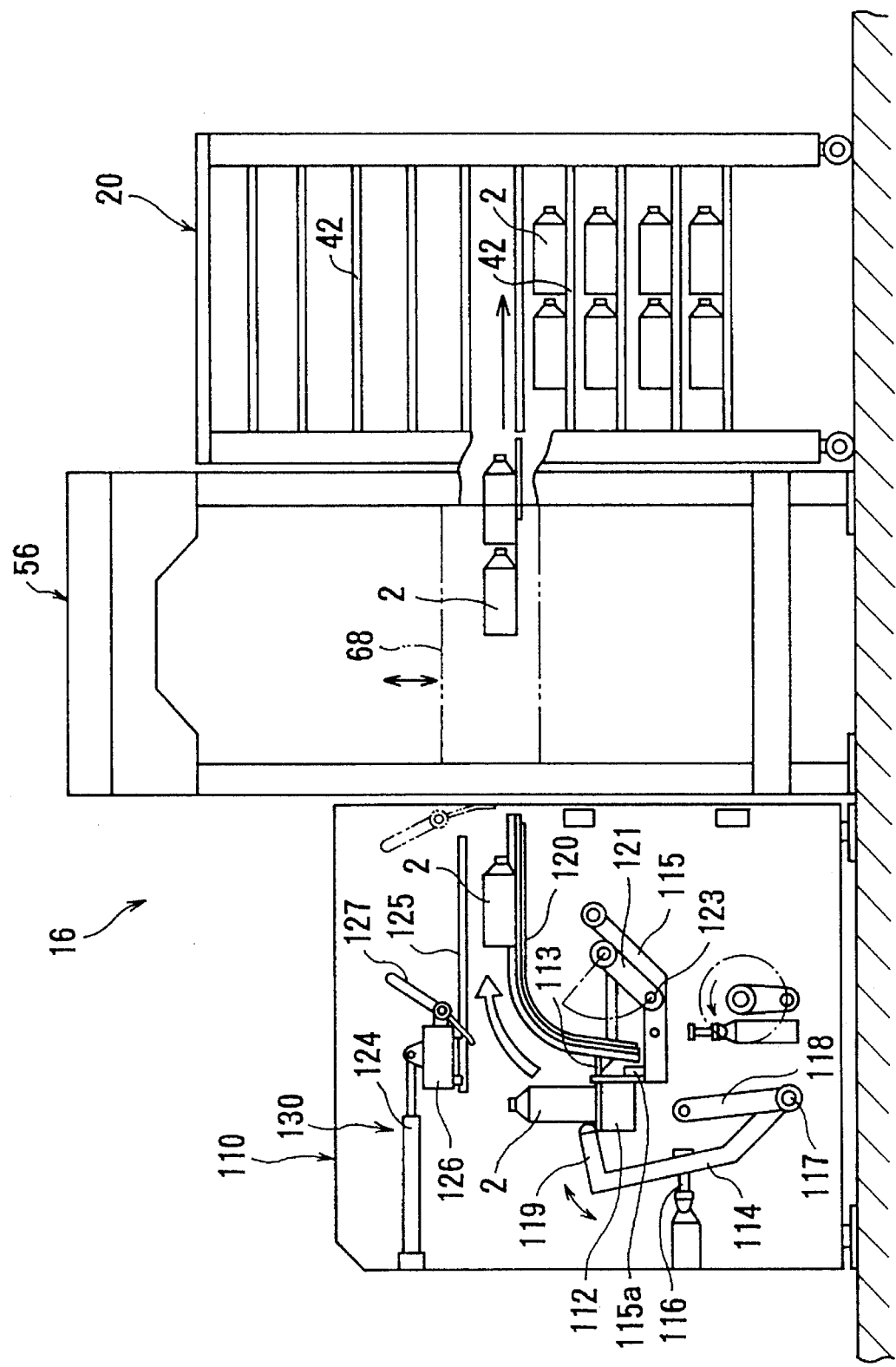
FIG. 7 is a side elevational view of a roller bottle charger and a roller bottle transfer device in a loading station.

As shown in FIG. 7, the loading station 16 comprises a roller bottle charger 110 and a roller bottle transfer device 56. The roller bottle transfer device 56 is identical to the roller bottle transfer device 56 shown in FIG. 5, and will not be described in detail below. The roller bottle charger 110 and the roller bottle transfer device 56 are positioned adjacent to each other, and culture racks 20 are positioned next to the roller bottle transfer device 56 remotely from the roller bottle charger 110.

As shown in FIG. 7, the roller bottle charger 110 comprises a first swing arm 114 for pushing roller bottles 2 delivered in an erected condition by the conveyor 112 onto a receiver base 113, a second swing arm 115 for lifting the roller bottles 2 from the receiver base 113 along a guide 120 to an uppermost position on the guide 120 in which the roller bottles 2 are in a recumbent or horizontal position, and a bottle pusher device 130 for pushing the roller bottles 2 into the base unit 68 of the roller bottle transfer device 56.

The first swing arm 114 has an end coupled by a pin 117 to a crank arm 118 which is angularly movable by a given angle by an actuator (not shown). The first swing arm 114 is swingable through a certain angle limited by a limiter 116 which engages an intermediate portion of the first swing arm 114. The first swing arm 114 has a pusher 119 on its distal end which is angularly movable with the first swing arm 114 from a position in which it abuts against the roller bottles 2 on the conveyor 112 to a position in which it pushes the roller bottles 2 onto the receiver base 113.

The second swing arm 115 has a lifting member 115a on its distal end for engaging the bottoms of the roller bottles 2 on the receiver base 113. A crank arm 121 is coupled to the second swing arm 115 by a pin 123. The crank arm 121 is angularly movable through 90° by an actuator (not shown). When the crank arm 121 is rotated clockwise, the second swing arm 115 lifts roller bottles 2 erected on the receiver base 113 along the guide 120. The guide 120 has an arcuate guide path extending arcuately along a quarter arc. As the roller bottles 2 are lifted along the guide 120, they are converted from the vertical position into the horizontal position on the upper surface of the guide 120, after which the bottle pusher device 130 starts to operate.

The bottle pusher device 130 basically comprises a cylinder 124 and a slider 126 movable back and forth along a guide rail 125 by the cylinder 124. A bottle stopper 127 is angularly movably supported on the distal end of the slider 126. When the slider 126 is moved forwardly by the cylinder 124 toward the roller bottle transfer device 56, the distal end of the bottle stopper 127 abuts against the bottoms of the roller bottles 2 which have been positioned horizontally on the uppermost surface of the guide 120. Continued forward movement of the slider 126 displaces the roller bottles 2 into the base unit 68 of the roller bottle transfer device 56.

After having received the roller bottles 2, the base unit 68 vertically moves to a position horizontally aligned with any empty culture shelf 42 of the culture rack 20, and pushes the roller bottles 2 stored therein into the empty culture shelf 42 of the culture rack 20.

The above operation of the loading station 16 is repeated to store successive arrays of roller bottles 2 into culture shelves 42 of the culture rack 20. When all the culture shelves 42 of the culture rack 20 are charged with roller bottles 2, the culture rack 20 is transferred onto an automatic guided vehicle 22. The culture rack 20 is then delivered into a predetermined storage location in the culture rack storage station 10.

Next, the whole operation of the roller bottle handling system will be described with reference to FIGS. 1 through 7. The culture rack 20 which stores a number of roller bottles 2 with completed cultures is delivered from the culture rack storage station 10 to the first transfer station 13 by the automatic guided vehicle 22. The culture rack 20 which has been unloaded from the automatic guided vehicle 22 at the first transfer station 13 is conveyed to the unloading station 12 by the aerial carriage 46.

In the unloading station 12, the roller bottles 2 are transferred by the roller bottle pusher device 54 from each of the culture shelves 42 of the culture rack 20 to the movable bed unit 68 of the roller bottle transfer device 56. The roller bottles 2 are then pushed out from the movable bed unit 68 onto the receiver base 86 of the roller bottle discharger 58. In the roller bottle discharger 58, the roller bottles 2 on the receiver base 86 are turned from a horizontal position to a vertical position by a swinging motion of the swing arm 88. At the same time, the roller bottles 2 placed in the elected position of the receiver base 86 are pushed by the pusher 102 onto the conveyor 90 by the actuation of the link 104.

The roller bottles 2 thus supplied to the conveyor 90 are then delivered to the mass-handling facility 14. While roller bottles 2 are continuously fed through the mass-handling facility 14 by the conveyor 90, the caps are removed from the roller bottles 2 by the cap removing device 26, and then the cultured cells are extracted from the roller bottles 2 by the culture medium drawing device 28. Thereafter, the inner surfaces of the empty roller bottles 2 are cleaned by the bottle cleaning device 30, and a new culture medium is filled in the roller bottles 2 and cells to be cultured are inoculated into the roller bottles 2 by the culture medium filling device 32. The caps are attached to the roller bottles 2 by the cap tightening device 34. The roller bottles 2 with the replaced culture medium and cells are then delivered to the loading station 16 by the conveyor 112.

On the other hand, in the unloading station 12, all the roller bottles are taken out from the culture rack 20. The empty culture rack 20 is thereafter carried by the aerial carriage 46 along the delivery line 24 to the loading station 16 where it waits for roller bottles from the mass-handling facility 14 where cultivated cells are extracted from the roller bottles, the empty roller bottles are cleaned, and filled with a culture medium and cells.

The roller bottles 2 delivered to the loading station 16 by the conveyor 112 are turned from a horizontal position to a vertical position by the roller bottle charger 110 and then transferred to the movable bed unit 68 of the roller bottle transfer device 56. After having received the roller bottles 2, the base unit 68 pushes the roller bottles 2 stored therein into the empty culture shelf 42 of the culture rack 20. The above operation of the loading station 16 is repeated to store successive arrays of roller bottles 2 into the culture shelves 42 of the culture rack 20. When all the culture shelves 42 of the culture rack 20 are charged with roller bottles 2, the culture rack 20 is conveyed by the aerial carriage 46 from the loading station 16 to the second transfer station 13. Thereafter, the culture rack 20 is transferred onto the automatic guided vehicle 22. The culture rack 20 is then delivered into a predetermined storage location in the culture rack storage station 10.

As is apparent from the above description, the roller bottle handling system can automate a process of handling roller bottles 2 rack by rack, i.e., can automatically carry out the various steps of delivering the culture racks 20 into and out of the culture rack storage station 10, taking out the roller bottles 2 from the culture racks 20, charging the roller bottles 2 into the culture racks 20, extracting cultures from the roller bottles 2, cleaning the roller bottles 2, and filling a culture medium and cells in the roller bottles 2. Accordingly, the roller bottle handling system can handle a large number of roller bottles 2 automatically.

In the culture rack storage station 10, the culture racks 20 are positioned in neat arrays on the floor, and the cells in the roller bottles 2 are cultured. While the cells in the roller bottles 2 are being cultured, they are periodically inspected for any trouble by an operator. In the event of some accident happening on any one of the culture racks 20 or the roller bottles 2 stored therein, since the roller bottles 2 are stored in the culture racks 20, only the culture rack 20 which has problems or contains a problem roller bottle or bottles 2 can quickly be removed out of the roller bottle handling system without shutting off the entire roller bottle handling system.

A roller bottle handling system according to a second embodiment of the present invention will be described below with reference to FIG. 8. Those parts of the roller bottle handling system shown in FIG. 8 which are identical to those shown in FIGS. 1 through 7 are denoted by identical reference numerals, and will not be described in detail below.

The roller bottle handling system according to the embodiment employs overhead traveling cranes, instead of automatic guided vehicles, for delivering culture racks 20 from the culture rack storage station 10 to a transfer station.

Figure 8:
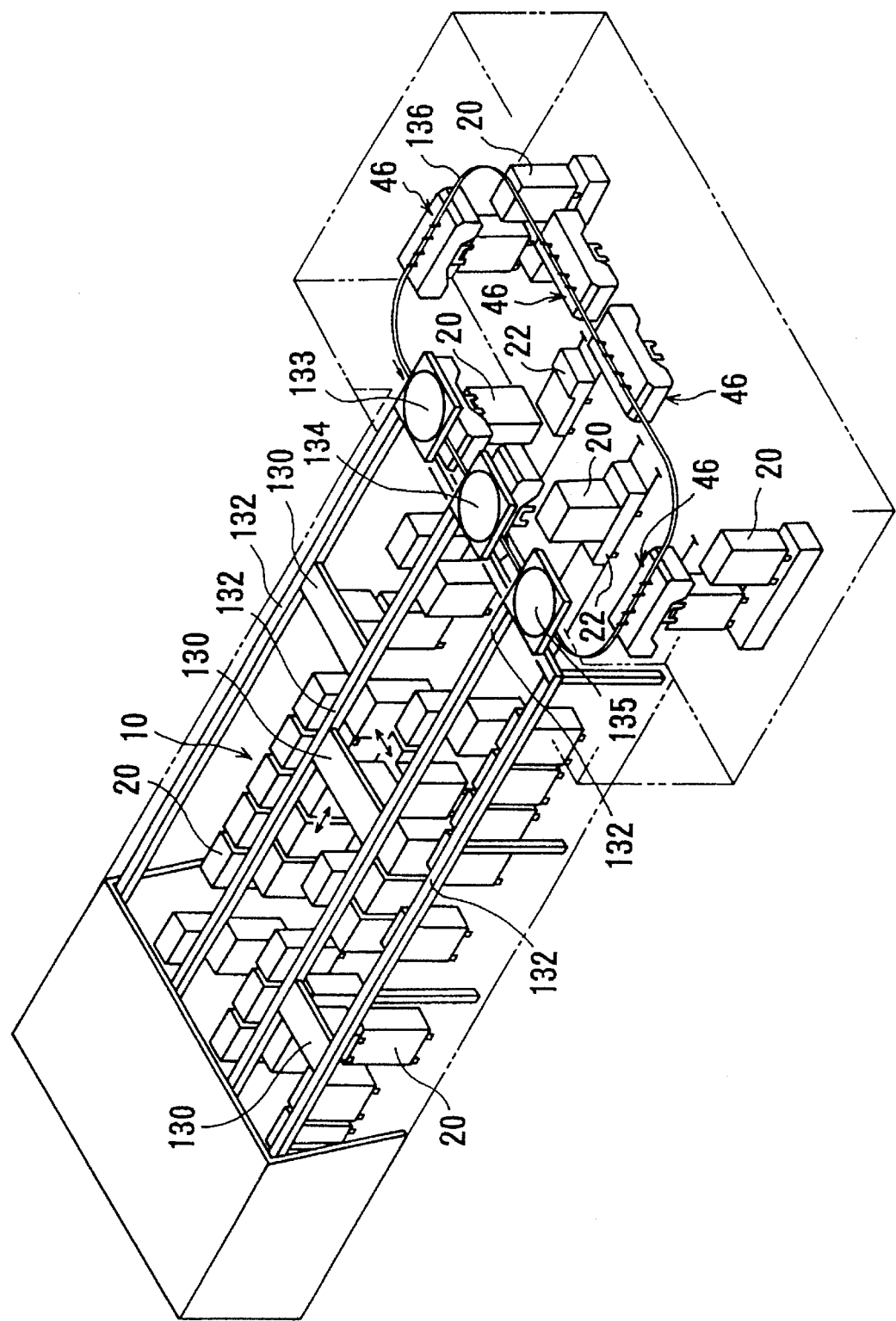
FIG. 8 is a perspective view of a roller bottle handling system according to a second embodiment of the present invention.

Specifically, as shown in FIG. 8, guide rails 132 are attached to the ceiling of the culture rack storage station 10 along arrays of culture racks 20, and overhead traveling cranes 130 are movable along the guide rails 132. There are three overhead traveling cranes 130 associated with the arrays of culture racks 20 and movable along the guide rails 132 to any position in the arrays of culture racks 20. Each of the overhead traveling cranes 130 has a hoist (not shown) movable in a direction perpendicular to the longitudinal direction of the guide rails 132. The roller bottle handling system also includes a plurality of transfer stations 133, 134, 135 at ends of the guide rails 132.

In the transfer stations 133, 134, 135, culture racks 20 are transferred onto aerial carriages 46 which run along an annular elevated track 136. Each of the aerial carriages 46 is identical to the aerial carriage 46 employed in the roller bottle handling system shown in FIGS. 1 through 7, and serves to deliver a culture rack 20 to an unloading station (not shown) where the roller bottles are taken out from the culture rack 20. The empty culture rack 20 are then delivered by an aerial carriage 46 to a loading station (not shown) where roller bottles with a replaced culture medium and cells are charged into the empty culture rack 20 by a roller bottle charger. The charged culture rack 20 is then delivered by an aerial carriage 46 to any one of the transfer stations 133, 134, 135, from which the culture rack 20 is delivered by one of the overhead traveling cranes 130 to a given location in the culture rack storage station 10.

The roller bottle handling system according to the embodiment shown in FIG. 8 may additionally employ automatic guided vehicles 22 as auxiliary carriages in the culture rack storage station 10.

The roller bottle handling system according to the second embodiment shown in FIG. 8 offers the same advantages as those of the roller bottle handling system according to the first embodiment shown in FIGS. 1 through 7.

A roller bottle handling system according to a third embodiment of the present invention will be described below with reference to FIG. 9. Those parts of the roller bottle handling system shown in FIG. 9 which are identical to those shown in FIGS. 1 through 7 are denoted by identical reference numerals, and will not be described in detail below.

Figure 9:
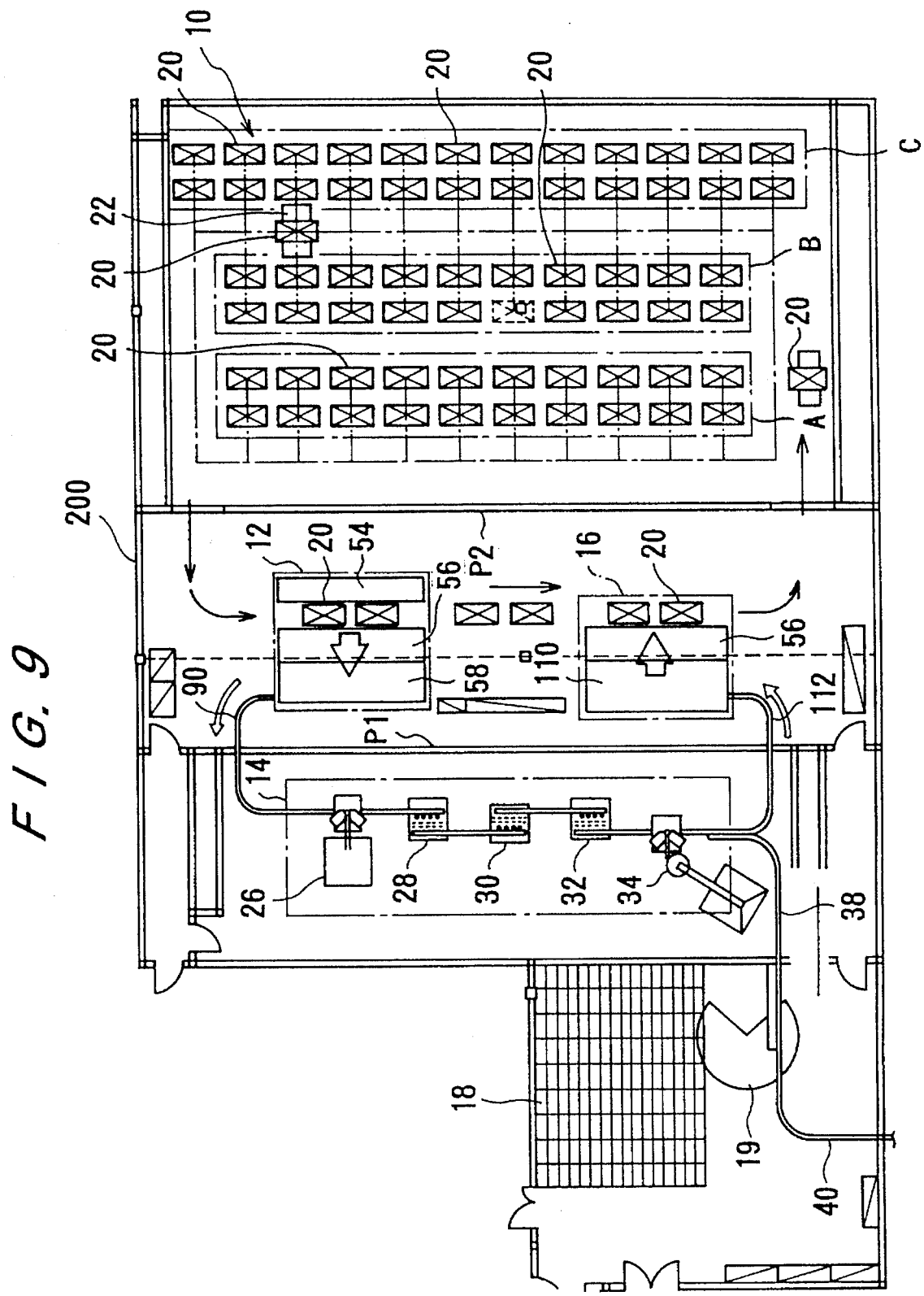
FIG. 9 is a plan view of a roller bottle handling system according to a third embodiment of the present invention.

In this embodiment, the culture racks 20 are carried by automatic guided vehicles 22 which run along the passageways between the arrays of culture racks 20 to deliver the culture racks 20 into and out of the culture rack storage station 10 in the direction indicated by the arrows in FIG. 9. To deliver a culture rack 20 out of the culture rack storage station 10, the culture rack 20 is placed on an automatic guided vehicle 22 and carried thereby in the culture rack storage station 10 up to the unloading station 12. In the unloading station 12, all the roller bottles are taken out from the culture rack 20. The empty culture rack 20 is thereafter carried by the automatic guided vehicle 22 to the loading station 16 where it waits for roller bottles from the mass-handling facility 14. In the mass-handling facility 14, cultivated cells are extracted from roller bottles, the empty roller bottles are cleaned, and filled with a culture medium and cells. After the roller bottles from the mass-handling facility 14 are transferred to the culture rack 20 at the loading station 16, the culture rack 20 is then delivered by the automatic guided vehicle 22 to a predetermined location in the culture rack storage station 10. That is, in this embodiment, the automatic guided vehicle 22 constitutes a common conveying means and serves both as a first conveying means and a second conveying means.

In the above embodiments, the culture rack storage station 10 is defined into a plurality of areas A, B and C. The culture racks 20 accommodating roller bottles 2 into which cells are inoculated on a first inoculation day are stored at the same area, for example, A, and the culture racks 20 accommodating roller bottles 2 into which cells are inoculated on a second inoculation day different from the first inoculation day are stored at the same area, for example, B different from the area A. That is, since a different lot of culture racks are stored at the different area of the culture rack storage station 10, the culture racks can be managed reliably without being mixed promiscuously.

Further, as shown in FIG. 9, in case of installing a roller bottle handling system in a clean room 200, a first partition P1 is provided between the mass-handling facility 14 and the loading and unloading stations 12 and 16, and a second partition P2 is provided between the culture rack storage station 10 and the loading and unloading stations 12 and 16. Openings are formed on the first partition P1 to allow the roller bottles 2 to pass therethrough, and openings are formed on the second partition P2 to allow the culture rack 20 to pass therethrough.

With the above arrangement, the degree of cleanliness of the mass-handling facility 14, the degree of cleanliness of the culture rack storage station 10 and the degree of cleanliness of the loading and unloading stations 12 and 16 can differ from one another, in accordance with level of requirements for cleanliness. Since dust particles are mainly generated at the sliding contact portions of the loading and unloading stations 12 and 16, the partitions P1 and P2 can prevent the generated dust particles from being scattered toward the culture rack storage station 10 and the mass-handling facility 14.

Although certain preferred embodiments of the present invention has been shown and described in detail, it should be understood that various changes and modifications may be made therein without departing from the scope of the appended claims.

What is claimed is:

1. A roller bottle handling system comprising:

a culture rack storage station storing a plurality of culture racks each accommodating a plurality of roller bottles filled with a culture medium and cells;

a mass-handling facility extracting completed cultures from the roller bottles and replacing a culture medium in the roller bottles with a new culture medium;

an unloading station taking out roller bottles from the culture racks delivered from said culture rack storage station and delivering the roller bottles to said mass-handling facility;

a loading station charging roller bottles filled with a culture medium and cells into culture racks;

first conveying means for delivering the culture racks, one at a time, between said culture rack storage station and said unloading and loading stations; and second conveying means for delivering the culture racks, one at a time, between said unloading station and said loading station wherein said second conveying means comprises an elevated track, an aerial carriage movable along the elevated track and grip means detachably gripping a top portion of each of said culture racks.

2. A roller bottle handling system according to claim 1, wherein said first conveying means comprises one of an automatic guided vehicle and an overhead traveling crane.

3. A roller bottle handling system according to claim 1, wherein said first and second conveying means comprise a guided conveying means.

4. A roller bottle handling system according to claim 3, wherein said first guided conveying means comprise an automatic guided vehicle.

5. A roller bottle handling system according to claim 1, wherein said culture racks are arranged in a number of arrays directly on a floor in said culture rack storage station.

6. A roller bottle handling system according to claim 1, wherein said culture rack storage station is defined into a plurality of areas so that the stored culture racks are not intermixed.

7. A roller bottle handling system according to claim 1, further comprising:

a first partition provided between said mass-handling facility and said loading and unloading stations; and a second partition provided between said culture rack storage station and said loading and unloading stations.

8. A roller bottle handling system according to claim 1, wherein said grip means comprises a support frame having grip arms which detachably engage a top portion of said culture racks.

9. A roller bottle handling system according to claim 8, wherein said top portion of said culture racks comprise a top plate with which the grip arms engage and said culture racks comprise wheeled racks.

10. A roller bottle handling system comprising:

a culture rack storage station storing a plurality of culture racks each accommodating a plurality of roller bottles filled with a culture medium and cells;

a mass-handling facility extracting completed cultures from the roller bottles and replacing a culture medium in the roller bottles with a new culture medium;

an unloading station taking out roller bottles from the culture racks delivered from said culture rack storage station and delivering the roller bottles to said mass-handling facility;

a loading station charging roller bottles filled with a culture medium and cells into culture racks;

a first conveying mechanism delivering the culture racks, one at a time, between said culture rack storage station and said unloading and loading stations; and a second conveying mechanism delivering the culture racks, one at a time, between said unloading station and said loading station wherein said second conveying mechanism comprises an elevated track, an aerial carriage movable along the elevated track and a grip mechanism detachably gripping a top portion of each of said culture rack.

11. A roller bottle handling system according to claim 10, wherein said first conveying mechanism comprises one of an automatic guided vehicle and an overhead traveling crane.

12. A roller bottle handling system according to claim 10, wherein said first and second conveying mechanism comprise a guided conveying mechanism.

13. A roller bottle handling system according to claim 12, wherein said first guided conveying mechanism comprises an automatic guided vehicle.

14. A roller bottle handling system according to claim 10, wherein said culture racks are arranged in a plurality of arrays directly on a floor in said culture rack storage station.

15. A roller bottle handling system according to claim 10, wherein said culture rack storage station is divided into a plurality of areas so that the stored culture racks are not intermixed.

16. A roller bottle handling system according to claim 10, further comprising:

a first partition provided between said mass-handling facility and said loading and unloading stations; and a second partition provided between said culture rack storage station and said loading and unloading stations.

17. A roller bottle handling system according to claim 10, wherein said grip mechanism comprises a support frame having grip arms which detachably engage a top portion of said culture racks.

18. A roller bottle handling system according to claim 17, wherein said top portion of said culture racks comprise a top plate with which the grip arms engage and said culture racks comprise wheeled racks.

* * * * *